US010024822B2

(12) United States Patent
Chatellier et al.

(10) Patent No.: US 10,024,822 B2
(45) Date of Patent: Jul. 17, 2018

(54) METHOD FOR CHARACTERISING A PART MADE OF A COMPOSITE MATERIAL

(71) Applicant: SNECMA, Paris (FR)

(72) Inventors: Jean-Yves François Roger Chatellier, Arcueil (FR); Nicolas Broussais-Colella, Melun (FR); Jérémy Duval, Juvisy sur Orge (FR); Jérémy Nicolas Marquis, Brest (FR); Anne Meyer, Sucy en Brie (FR)

(73) Assignee: SNECMA, Paris (FR)

( * ) Notice: Subject to any disclaimer, the term of this patent is extended or adjusted under 35 U.S.C. 154(b) by 192 days.

(21) Appl. No.: 14/652,593

(22) PCT Filed: Dec. 6, 2013

(86) PCT No.: PCT/FR2013/052985
§ 371 (c)(1),
(2) Date: Jun. 16, 2015

(87) PCT Pub. No.: WO2014/096617
PCT Pub. Date: Jun. 26, 2014

(65) Prior Publication Data

US 2015/0330949 A1 Nov. 19, 2015

(30) Foreign Application Priority Data

Dec. 17, 2012 (FR) ..................................... 12 62155

(51) Int. Cl.
*G01N 29/04* (2006.01)
*G01N 29/11* (2006.01)
(Continued)

(52) U.S. Cl.
CPC ........... *G01N 29/043* (2013.01); *G01N 29/07* (2013.01); *G01N 29/11* (2013.01); *G01N 29/28* (2013.01);
(Continued)

(58) Field of Classification Search
CPC ...... G01N 29/043; G01N 29/07; G01N 29/28; G01N 29/46; G01N 29/11; G01B 17/02
See application file for complete search history.

(56) References Cited

U.S. PATENT DOCUMENTS 3,930,404 A * 1/1976 Ryden, Jr. .............. G01B 17/02 73/610
4,049,954 A * 9/1977 Da Costa Vieira .... G01B 17/00 367/7

(Continued)

FOREIGN PATENT DOCUMENTS

DE 4233958 A1 4/1994
FR 2 959 817 A1 11/2011

(Continued)

OTHER PUBLICATIONS

Search Report dated Apr. 14, 2014, in corresponding International Application No. PCT/FR2013/052985, filed on Dec. 6, 2013 (3 pages).

(Continued)

*Primary Examiner* — Helen Kwok
(74) *Attorney, Agent, or Firm* — Bookoff McAndrews, PLLC

(57) ABSTRACT

The invention consists in a method of characterizing a part made of composite material (30), the method comprising a step of determining a characteristic of a longitudinal ultrasound wave (41) traveling along a path within the part (30), and being characterized in that the travel time of a longitudinal ultrasound wave (42) transmitted by the part (30) is measured (E4).

6 Claims, 3 Drawing Sheets

(51) Int. Cl.
*G01N 29/28* (2006.01)
*G01N 29/46* (2006.01)
*G01N 29/07* (2006.01)

(52) U.S. Cl.
CPC ..... *G01N 29/46* (2013.01); *G01N 2291/0231* (2013.01); *G01N 2291/048* (2013.01); *G01N 2291/0421* (2013.01)

(56) References Cited

U.S. PATENT DOCUMENTS 4,254,660 A * 3/1981 Prause .................. G01B 17/00 73/597
4,404,853 A * 9/1983 Livingston ............ E21B 17/006 73/622
4,515,545 A 5/1985 Hinrichs et al.
4,520,670 A * 6/1985 Salomonsson ......... G01N 29/30 73/602
4,625,555 A * 12/1986 Fujii ...................... G01N 29/07 73/597
5,009,103 A * 4/1991 Sato ....................... G01B 17/02 702/171
5,052,227 A * 10/1991 Le Floc'H ............. G01B 17/02 73/597
5,072,388 A * 12/1991 O'Sullivan et al. ..... G01V 1/50 181/105
5,115,681 A * 5/1992 Bouheraoua ........... G01N 29/07 73/643
5,156,636 A * 10/1992 Kuljis .................... G01B 17/02 73/597
5,170,367 A * 12/1992 Mackay ................. G01N 29/30 702/22
5,181,421 A 1/1993 Kline
5,201,225 A * 4/1993 Takahashi ............. G01B 17/02 73/615
5,408,882 A 4/1995 McKinley et al.
5,448,915 A * 9/1995 Dunn ................... G01B 17/025 73/597
5,596,508 A * 1/1997 Cuffe ..................... G01B 17/02 702/171
5,661,241 A * 8/1997 Harth, III ............. G01B 17/025 702/171
5,824,908 A 10/1998 Schindel et al.
6,534,964 B1 * 3/2003 Sinha ..................... G01N 29/50 324/71.1
6,634,233 B2 * 10/2003 He ......................... G01B 17/02 73/597
6,883,376 B2 * 4/2005 He ......................... G01B 17/02 73/597
7,140,253 B2 * 11/2006 Merki .................... G01N 29/07 73/620
8,857,269 B2 * 10/2014 Johnson ............ A61M 5/16877 604/151
2002/0134157 A1 * 9/2002 Chatellier ............. G01N 29/07 73/579
2005/0186328 A1 * 8/2005 Chatellier ............. G01N 19/04 427/8
2009/0277269 A1 11/2009 Sarr
2010/0107768 A1 * 5/2010 Elze ..................... G01N 29/043 73/627
2013/0098157 A1 * 4/2013 Suzuki .................... G01S 7/521 73/597
2014/0000372 A1 * 1/2014 Bessri .................... G01N 29/24 73/644
2014/0318251 A1 * 10/2014 Chatellier ............. G01N 29/07 73/597
2015/0198565 A1 * 7/2015 Chatellier ............. G01N 29/04 73/597

FOREIGN PATENT DOCUMENTS

JP H03503312 A 7/1991
JP H05172793 A 7/1993
JP H05192332 A 8/1993
JP H06174455 A 6/1994
JP H07260751 A 10/1995
JP 2007139784 A 6/2007
RU 2280251 C1 7/2006
WO WO 89/06796 7/1989

OTHER PUBLICATIONS

Office Action and Search Report dated Apr. 12, 2017, in corresponding Russian Application No. 2015129071 (12 pages).
English translation of Office Action dated Oct. 3, 2017, in corresponding Japanese Application No. 2015-547114 (4 pages).

* cited by examiner

METHOD FOR CHARACTERISING A PART MADE OF A COMPOSITE MATERIAL

This application is the U.S. national phase entry under 35 U.S.C. § 371 of International Application No. PCT/FR2013/052985, filed on Dec. 6, 2013, which claims priority to French Patent Application No. FR 1262155, filed on Dec. 17, 2012, the entireties of each of which are incorporated by reference herein.

TECHNICAL FIELD AND PRIOR ART

The invention lies in the field of methods of characterizing parts made of composite material, in the engineering industry, and in particular in the aviation industry.

While a given part is being developed, it is necessary to know the fiber content and the resin content in a given zone of the part. To do this, it is known to measure the propagation speed and the attenuation of a longitudinal ultrasound wave passing through the part.

One method of measuring these magnitudes is to use an ultrasound transducer in transceiver mode. Attention is then given to a zone of the part that is defined by mutually parallel front and back surfaces. The longitudinal wave is directed so as to propagate orthogonally to the two surfaces, being partially reflected and also being attenuated in the material of the part. There are thus observed a first echo, coming from the front surface, and a second echo coming from the back surface and referred to as the back echo. The transducer receives the reflected wave, and it is then possible by observing the two reflected components to deduce both the propagation speed and the attenuation of the wave in the material.

Nevertheless, that solution is unsuitable for materials that absorb ultrasound waves strongly. This applies for example to three-dimensional 3D woven composites of a structure that is inhomogeneous and anisotropic. For parts of industrial thicknesses, no back echo is visible in recordings made on those materials, because of the strong absorption.

It is thus necessary to develop a method suitable for application to parts made of composite materials and enabling a large number of parts to be characterized, independently of their thickness or of their absorbent nature.

Definition of the Invention and Associated Advantages

The invention relates to a method of characterizing a part made of composite material, the method comprising a step of determining a characteristic of a longitudinal ultrasound wave traveling along a path within the part, and being characterized in that the travel time of a wave transmitted by the part is measured.

By means of this technique, the problem associated with the absence of a back echo in transceiver mode measurements is overcome.

According to an advantageous characteristic, the travel time of the transmitted wave is measured by observing the beginning of the wave.

By means of this characteristic, it is possible to ignore greatly amplified problems of phase shifting and of deformation of the sinusoidal signal of the ultrasound wave used, as caused by thick materials, or as caused by the complex, inhomogeneous, and anisotropic structure of certain composite materials.

In an implementation, the propagation speed of the longitudinal ultrasound wave following a path in the part is determined.

This provides information that is useful for determining the fiber content and the resin content of a composite material, which information can be used in the development of the part under study.

In another implementation, which may be combined with the preceding implementation, the amplitude of the transmitted wave is also measured in order to determine the overall or unit length attenuation to which the longitudinal ultrasound wave is subjected on traveling in the part.

This provides information that is useful for determining the pore content, which can be used in the development of the part under study.

Preferably, the propagation time of an ultrasound wave transmitted in the absence of the part is measured, as are the propagation times of ultrasound waves reflected respectively by a first face of the part and by a second face of the part, in order to determine the dimension of the part passing the longitudinal ultrasound wave traveling along a path in the part.

By means of this characteristic, which is optional but advantageous, an accurate measurement is obtained of the dimension of the part that passes the transmitted wave, whereas such a dimension is quite variable in parts made of composite material, so it can therefore be useful to know an exact value for a given part, for the particular path followed by the ultrasound wave used.

In particular, the method is performed for a part made of 3D woven composite material.

Such materials are particularly challenging to characterize because of their inhomogeneity and because of their anisotropy. By means of the invention, it is possible to study them quickly and reliably, particularly while parts are under development.

DETAILED DESCRIPTION OF AN IMPLEMENTATION

Figure 1:
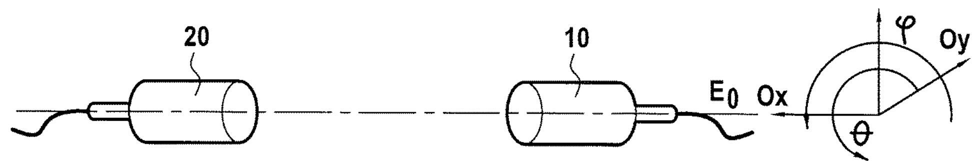
FIG. 1 shows a preliminary operation in the context of performing a method of the invention.

With reference to FIG. 1, two plane ultrasound sensors operating in transmission mode are put into alignment. This putting into alignment constitutes a preliminary step E0. The sensors are separated by a liquid, such as water. The transducer 10 operates in emission mode, and the sensor 20 in reception mode. The signal received by the sensor 20 passes through a maximum after successive adjustments of the axes Oy and Oz, and also the angles θ and φ.

Figure 2:
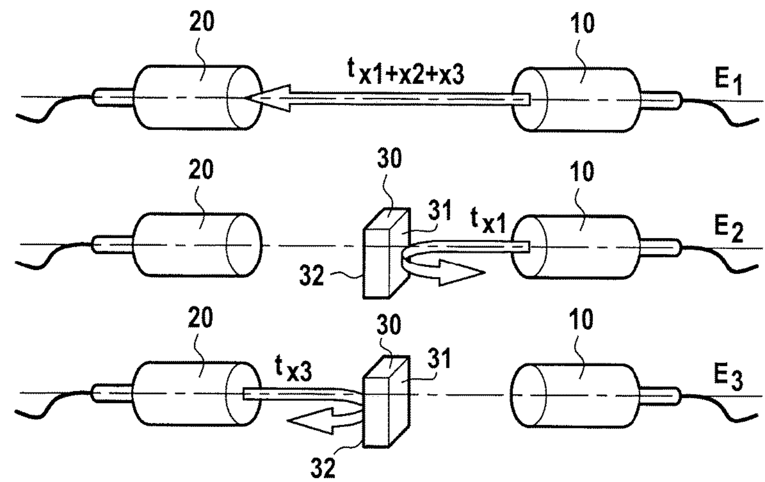
FIG. 2 shows the three steps of a thickness measuring stage performed in the invention.

In FIG. 2, a measurement is made of the thickness of the material of the part under study, referenced 30. The measurement needs to be accurate to within one micrometer.

A first step E1 consists in measuring the travel time of the wave transmitted through the water between the two transducers 10 and 20, in the absence of the part. A second step consists in measuring the travel time of the wave reflected by the first surface, referenced 31, of the part 30, with the transducer 10 operating as a transceiver and facing the surface 31. A third step consists in measuring the travel time of the wave reflected by the second surface, referenced 32, of the part 30, with the transducer 20 operating in turn as a transceiver and facing the surface 32.

The travel time is measured on each occasion by observing the beginning of the signal, and not an arch of the signal. This makes it possible for the operator to ignore any phenomenon associated with possible phase shifting of the signal. Specifically, in the presence of multiple reflections, phase shifts appear. This also happens when, after a reflection, the signal is inverted. The shape of the arches of the signal is modified, and it is difficult to obtain an accurate value for the travel time. That is why it is proposed to measure the signal by observing solely the beginning of the signal.

Since the propagation speed of the wave in water $V_{water}$ is known, it is possible by subtraction to obtain the thickness of the part from the steps E1, E2, and E3, by using the formula $X_2=(t_{X1+X2+X3}-t_{X3}-t_{X1})\times V_{water}$, where X1 is the distance between the transducer 10 and the surface 31, X2 is the thickness of the part at the point of impact of the beam, and X3 is the distance between the transducer 20 and the surface 32, and where $t_{X1+X2+X3}$, $t_{X1}$ and $t_{X3}$ are the travel times measured during the steps E1, E2, and E3 respectively.

Figure 3:
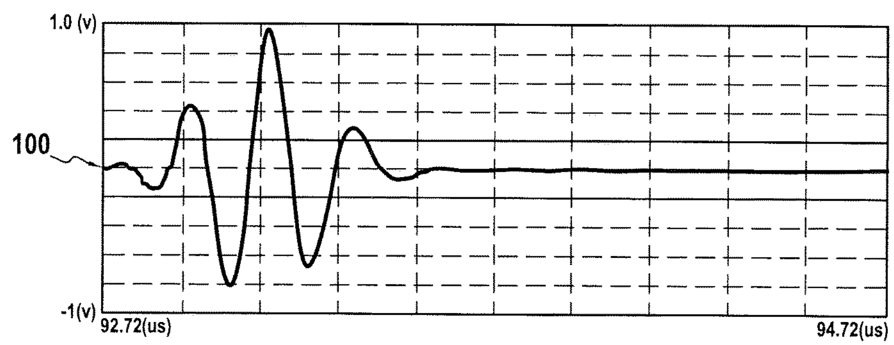
FIGS. 3 to 5 show the signals recorded during the three steps of FIG. 2.
Figure 4:
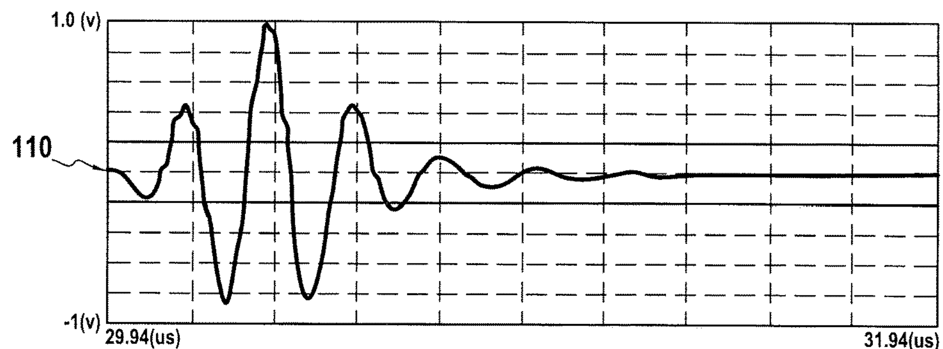
Figure 5:
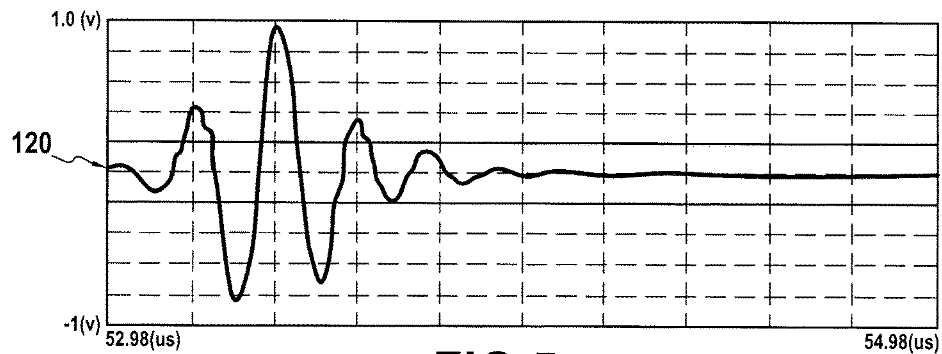

FIGS. 3 to 5 show the plots displayed during steps E1, E2, and E3 respectively, with water at 22° C., a wave at a frequency of 5 megahertz (MHz) (giving a propagation speed of 1486.45 meters per second (m/s) in water), for a spacer having a thickness of 76.20 millimeters (mm) and made of TA6V titanium. The travel time of the wave is measured on the basis of the beginning of the wave, given respective references 100, 110, and 120.

The following results are obtained:

$t_{X1+X2+X3}=92.72$ microseconds (µs)

$t_{X3}=52.98/2=26.49$ µs $t_{X1}=29.94/2=14.97$ µs $X2=(t_{X1+X2+X3}-t_{X3}-t_{X1})\times V_{water}$ $X2=(92.72\times10^{-6}-26.49\times10^{-6}-14.97\times10^{-6})\times1486.54$ X2=76.20 mm The thickness measured with calipers is indeed 76.20 mm, i.e. 3".

Figure 6:
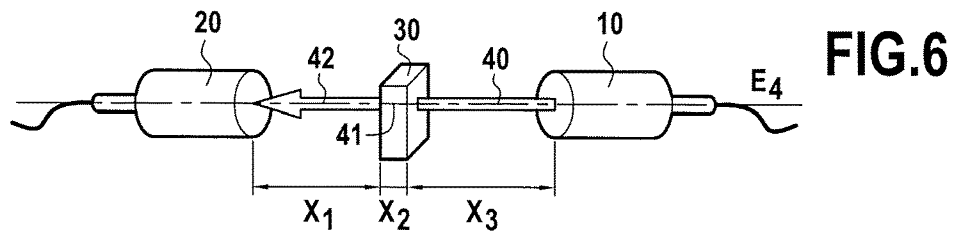
FIG. 6 shows the step of observing a transmitted wave, during a method of the invention.

FIG. 6 shows the step E4 during which the wave transmitted by the part 30 is observed. Thus, the transducer 10 is operating in emitter mode, while the transducer 20 is operating in receiver mode. The incident wave is referenced 40 in the figure, the wave propagating in the part 30 is referenced 41, and the transmitted wave is referenced 42.

The travel time of the wave in the part 30 is expressed in the form $t'_{X2}=t-(t_{X1}+t_{X3})$. Knowing X2 as determined beforehand, the propagation speed of the wave in the material is expressed in the form $V_{material}=X2/t'_{X2}$.

Figure 7:
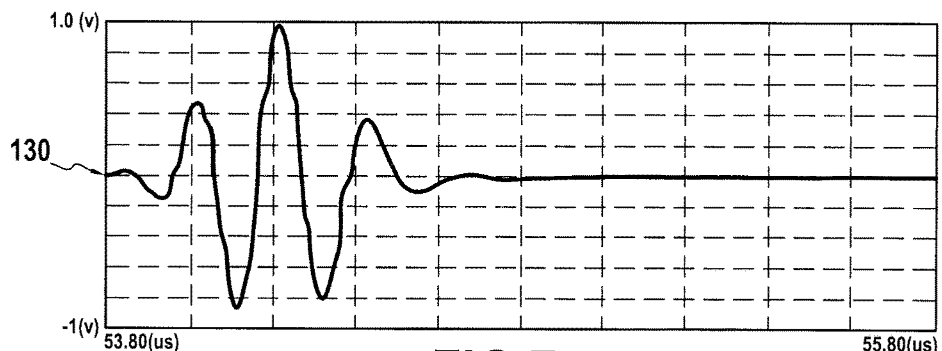
FIG. 7 shows the signal measured during the step of FIG. 6.

FIG. 7 shows the signal observed during the step E4 for the 76.20 mm thick space spacer made of titanium (TA6V), still with a wave at 5 MHz. The travel time of the wave is measured on the basis of the beginning of the wave, referenced 130.

The values obtained are as follows:

$t=53.80$ µs $t'_{X2}=(53.80\times10^{-6}-26.49\times10^{-6}-14.97\times10^{-6})$ $t'_{X2}=12.34$ µs $V=76.20\times10^{-3}/12.34\times10^{-6}$ And finally, the numerical value of the speed is V=6175.04 m/s. This value is verified with a conventional propagation speed measurement in order to validate the method.

Figure 8:
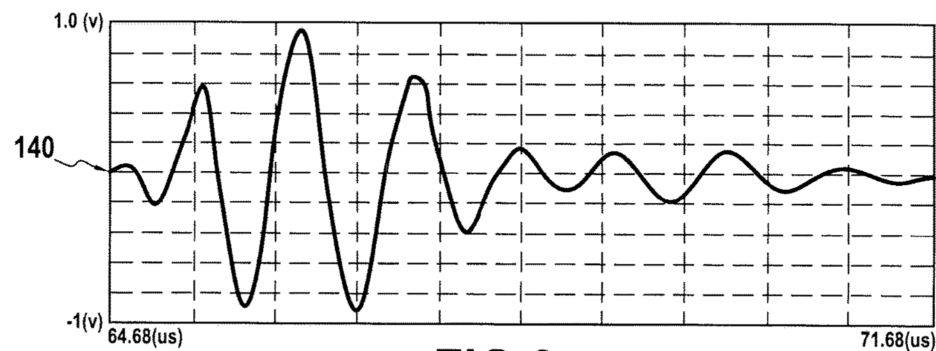
FIGS. 8 to 10 show signals obtained during the steps of FIGS. 2 and 6 for a spacer made of composite material.
Figure 9:
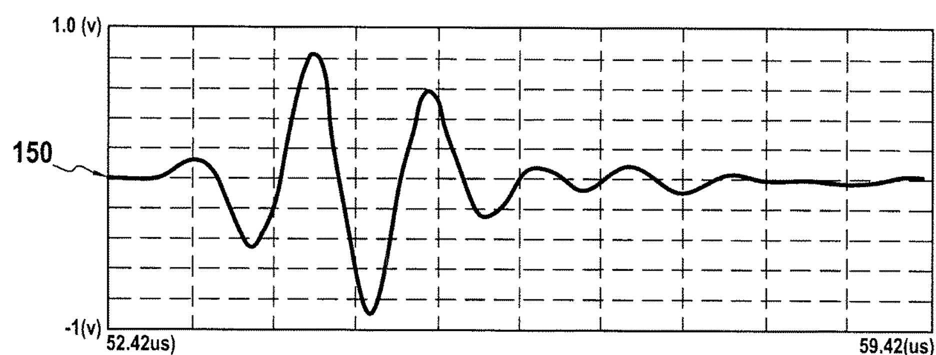
Figure 10:
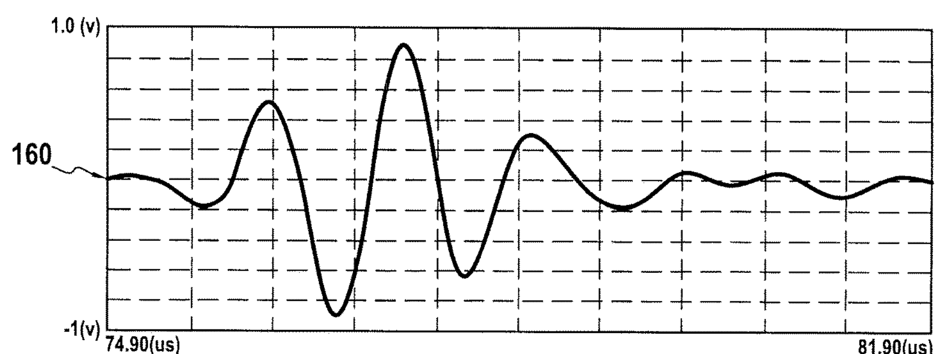

FIGS. 8 to 10 show the scans obtained for the steps E2, E3, and E4 for a composite stepped spacer having a thickness of 47.09 mm, with a transducer emitting at 1 MHz. The travel time of the wave is measured on the basis of the beginnings of the waves, given respective references 140, 150, and 160.

The values obtained are as follows:

$t_{X1+X2+X3}=90.22$ µs $t=74.90$ µs $t_{X3}=52.42/2=26.21$ µs $t_{X2}=64.68/2=32.34$ µs $X2=t_{X1+X2+X3}-t_{X3}-t_{X1})\times V_{water}$ $X2=(90.22\times10^{-6}-26.21\times10^{-6}-32.34\times10^{-6})\times1486.54$ $X2=31.67\times10^{-6}\times1488.76$ X2=47.078 mm $t'_{X2}=t-(t_{X1}+t_{X3})$ $t'_{X2}=(74.90\times10^{-6}-26.21\times10^{-6}-32.34\times10^{-6})$ $t+_{X2}=16.35$ µs $V_{composite}=X2/t'_{X2}$ $V_{composite}=47.078\times10^{-3}/16.35\times10^{-6}$ And finally, the numerical value of the speed is $V_{composite}=2879.4$ m/s.

Attention is then given to the attenuation of the longitudinal wave in the material.

The expression for the amplitude of the wave transmitted from the emitter to the receiver is written as follows: $Y_1=A_{max}e^{-\alpha1.(X1+X2+X3)}$, where $A_{max}$ represents the maximum amplitude at the surface of the transducer and $\alpha_1$ is the attenuation of the wave in water.

The expression for the amplitude of the wave transmitted from the emitter to the receiver after passing through the material is written as follows: $Y_2=A_{max}e^{-\alpha1(X1+X3)}e^{-\alpha2X2}t_{12}t_{21}$, where $\alpha_2$ is the attenuation of the wave in the material, $t_{12}$ is the amplitude transmission coefficient from water to the material, and $t_{21}$ is the amplitude transmission coefficient from the material to water.

The expression for the product $t_{12}\times t_{21}$ is a function of the acoustic impedance of the material $Z_2=\rho_2\times V_2$ and of the acoustic impedance of water $Z_1=\rho_1\times V_1$. In the acoustic impedance expression, ρ represents density and V represents the propagation speed of the longitudinal wave at the frequency under consideration.

$$t_{12}t_{21}=\frac{4\cdot Z_1Z_2}{(Z_1+Z_2)^2}$$

The amplitude ratio $Y_1/Y_2$ is written as follows:

$$\frac{Y_1}{Y_2}=\frac{e^{-\alpha1X2}}{e^{-\alpha2X2}\cdot t_{12}t_{21}}.$$

From which it is possible to deduce the expression for attenuation in the material:

$$\alpha_2=\frac{1}{x_2}\left(\mathrm{Ln}\left(\frac{Y_1}{Y_2}\cdot t_{12}t_{21}\right)+\alpha_1x_2\right).$$

A first implementation relates to the spacer of composite material having thickness of 47.09 mm, using a wave at 2.25 MHz.

The numerical values for this implementation are as follows:

$\rho_2$=1525.71 kilograms per cubic meter (kg/m$^3$)
$V_2$=2946.75 m/s
$Z_2$=4.39316 megOhms alternating current (M$\Omega_{ac}$)
$\rho_{water}$=997.77 kg/m$^3$
$V_{water}$=1486.54 m/s
$Z_{water}$=1.48322 M$\Omega_{ac}$
$t_{12}\times t_{21}$=0.75478
$x_2$=47.078 mm (accurate ultrasound measurement)
$Y_1$=643.2 millivolts (mV)
$Y_2$=15.885 mV
$\alpha_{water2.25MHz}$=0.972 nepers per meter (Np/m)
$\alpha_2$=73.61 Np/m.

A second implementation relates to the spacer of composite material having thickness of 47.09 mm, using a wave at 1 MHz.

$\rho_2$=1525.71 kg/m$^3$
$V_2$=2879.39 m/s
$Z_2$=4.39311 M$\Omega_{ac}$
$\rho_{water}$=997.77 kg/m$^3$
$V_{water}$=1486.54 m/s
$Z_{water}$=1.48322 M$\Omega_{ac}$
$t_{12}\times t_{21}$=0.75479
$x_2$=47.078 mm (accurate ultrasound measurement)
$Y_1$=370.25 mV
$Y_2$=16.395 mV
$\alpha_{water1MHz}$=0.682 Np/m
$\alpha_2$=60.92 Np/m.

The invention is not limited to the implementations described but extends to any variant within the scope of the claims.

The invention claimed is:

1. A method of characterizing a part made of composite material, the method comprising a step of determining a characteristic of a longitudinal ultrasound wave traveling along a path within the part, and being characterized in that a travel time of a longitudinal ultrasound wave transmitted by the part is measured, and the travel time of the transmitted wave is measured by observing the beginning of the transmitted wave, wherein a propagation time of an ultrasound wave transmitted through a liquid in the absence of the part is measured, and the propagation times of ultrasound waves reflected respectively by a first face of the part and by a second face of the part are measured with a first transducer facing the first face and a second transducer facing the second face of the part in order to determine a dimension of the part traveled by the longitudinal ultrasound wave traveling along the path within the part, wherein an amplitude of the transmitted wave is also measured in order to determine an overall or unit length attenuation to which the longitudinal ultrasound wave is subjected on traveling within the part, wherein an overall attenuation ($\alpha_2$) of the longitudinal ultrasound wave in the part is determined according to the following equation:

$$\alpha_2 = \frac{1}{x_2}\left(\text{Ln}\left(\frac{Y_1}{Y_2}\cdot t_{12}t_{21}\right) + \alpha_1 x_2\right)$$

where $Y_1/Y_2$ is an amplitude ratio, $t_{12}$ is an amplitude transmission coefficient from the liquid to the composite material, $t_{21}$ is an amplitude transmission coefficient from the composite material to the liquid, $\alpha$1 is a value of an attenuation of the transmitted wave in the liquid, and $x_2$ is the dimension of the part traveled by the transmitted wave traveling along the path within the part.

2. A method according to claim 1, wherein a propagation speed of the longitudinal ultrasound wave in the part following the path within the part is determined.

3. A characterization method according to claim 1, performed for a part made of 3D woven composite material.

4. A method according to claim 1, wherein $x_2$ is determined according to the equation:

$$x_2=(t_{X1+X2+X3}-t_{X3}-t_{X1})\times V_{liquid}$$

where $V_{liquid}$ is a propagation speed of the wave in the liquid, $t_{X1+X2+X3}$ is the propagation time of the ultrasound wave transmitted through the liquid in the absence of the part, $t_{X1}$ is the propagation time of the ultrasound wave reflected by the first face of the part, and $t_{X3}$ is the propagation time of the ultrasound wave reflected by the second face of the part.

5. A method according to claim 1, wherein $t_{12}t_{21}$ is determined according to the equation:

$$t_{12}t_{21} = \frac{4Z_1Z_2}{(Z_1+Z_2)^2}$$

where $Z_1$ is an acoustic impedance of the liquid, and $Z_2$ is an acoustic impedance of the composite material.

6. A method according to claim 5, wherein the acoustic impedance of the liquid, $Z_1$, and the acoustic impedance of the composite material, $Z_2$, are calculated according to equations:

$$Z_1=\rho_1\times V_1$$

$$Z_2=\rho_2\times V_2$$

where $\rho_1$ is a density of the liquid, $\rho_2$ is a density of the composite material, and $V_1$ is a propagation speed of the transmitted wave within the liquid, and $V_2$ is a propagation speed of the transmitted wave within the composite material.

* * * * *